United States Patent
Kobayashi et al.

(10) Patent No.: US 6,872,244 B2
(45) Date of Patent: Mar. 29, 2005

(54) PASTE TYPE DENTAL GLASS IONOMER CEMENT COMPOSITION

(75) Inventors: Keizo Kobayashi, Itabashi-ku (JP); Shinichi Kato, Itabashi-ku (JP)

(73) Assignee: GC Corporation, Tokyo (JP)

( * ) Notice: Subject to any disclaimer, the term of this patent is extended or adjusted under 35 U.S.C. 154(b) by 42 days.

(21) Appl. No.: 10/310,052

(22) Filed: Dec. 5, 2002

(65) Prior Publication Data

US 2003/0136303 A1 Jul. 24, 2003

(30) Foreign Application Priority Data

Dec. 17, 2001 (JP) ....................................... 2001-383273

(51) Int. Cl.$^7$ ................................................ A61K 6/06
(52) U.S. Cl. .......................... 106/35; 523/115; 523/116
(58) Field of Search ............................ 106/35; 523/115, 523/116

(56) References Cited

U.S. PATENT DOCUMENTS

| | | | |
|---|---|---|---|
| 5,063,257 A | 11/1991 | Akahane et al. | |
| 5,520,725 A | 5/1996 | Kato et al. | |
| 5,965,632 A | * 10/1999 | Orlowski et al. | ........... 523/116 |
| 6,214,101 B1 | 4/2001 | Nakaseko | |

* cited by examiner

*Primary Examiner*—C. Melissa Koslow
(74) *Attorney, Agent, or Firm*—Oblon, Spivak, McClelland, Maier & Neustadt, P.C.

(57) ABSTRACT

A paste type dental glass ionomer cement composition in paste type using no polymerizable monomer, that is good in operationality with excellent inherent characteristics of glass ionomer cement maintained, is constituted with a first paste and a second paste, in which the first paste contains 30 to 70% by weight of a polymer of an α-β unsaturated carboxylic acid and 30 to 70% by weight of water, and the second paste contains 50 to 85% by weight of fluoroaluminosilicate glass, 0.005 to 1% by weight of a water soluble thickening agent and the remaining percentage by weight of water, the mixing amount of the water soluble thickening agent being preferably 0.01 to 0.4% by weight.

12 Claims, No Drawings

PASTE TYPE DENTAL GLASS IONOMER CEMENT COMPOSITION

BACKGROUND OF THE INVENTION

1. Field of the Invention

The present invention relates to dental glass ionomer cement, and more particularly, it relates to a dental glass ionomer cement composition in paste form constituted from a first paste and a second paste, which are mixed to exert hardening.

2. Description of the Conventional Art

Various kinds of dental cement have been used for a wide range of purposes. Representative examples of dental cement that is currently used include zinc phosphate cement utilizing reaction between zinc oxide and phosphoric acid, polycarboxylate cement utilizing reaction between zinc oxide and polycarboxylic acid, zinc oxide eugenol cement utilizing reaction between zinc oxide and eugenol, glass ionomer cement utilizing reaction between fluoroaluminosilicate glass and polycarboxylic acid, and resin cement utilizing polymerization of an acrylic monomer.

These kinds of dental cement each have advantages and disadvantages. For example, the zinc phosphate cement has such problems that it has no adhesion property to teeth, and phosphoric acid causes irritation in the initial stage of hardening; the polycarboxylate cement has such problems that a set body thereof is low in hardness; and the zinc oxide eugenol cement has such problems that it is low in strength and is inferior in durability inside an oral cavity, whereby the purpose thereof is limited to temporary sealing and temporary adhesion, and also eugenol itself has acridity. The resin cement has such advantages that the other kinds of cement does not have, i.e., excellent adhesion property and excellent mechanical strength, but there are such problems that the operationality thereof is complicated, and there remain some problems in bio-compatibility.

The glass ionomer cement is used by hardening through reaction of an acid, such as a polycarboxylic acid, and fluoroaluminosilicate glass powder in the presence of water. The glass ionomer cement has such excellent characteristics that it has considerably good bio-compatibility, a set body thereof is translucent and is excellent in esthetics, it has excellent adhesion property to teeth, such as enamel and dentin, and it has an anti-dental caries function owing to fluoride contained in the glass. Owing the characteristics, the glass ionomer cement is widely used in the field of dental surgery for filling a cavity of dental caries, cementing of a crown-inlay-bridge and an orthodontic band, a lining of a cavity, a sealer for root canal, core construction, and pit and fissure sealing.

While the glass ionomer cement has various characteristics noted in the foregoing, the ordinary dental glass ionomer cement is constituted from a powder component and a liquid component and has disadvantages of complication in operations, such as quantitation and mixing. In view of the disadvantages, the inventors have proposed a glass ionomer cement composition in paste type constituted with a first paste containing a polycarboxylic acid, water and a filler that does not react with the polycarboxylic acid, and a second paste containing fluoroaluminosilicate glass powder and a polymerizable monomer having no acid group, to which a polymerization catalyst corresponding to the polymerization method for the polymerizable monomer is appropriately added, as disclosed in Japanese Patent Laid-Open No. JP228327/1999.

However, although the glass ionomer cement in paste type is excellent in mechanical strength owing to the use of the polymerizable monomer for providing the paste type of the components containing the fluoroaluminosilicate glass, there is a possibility of adverse affect of an unreacted monomer remaining after polymerization to a living body. Furthermore, a hydrophilic thickening agent is generally used in the case where components containing fluoroaluminosilicate glass but containing no polymerizable monomer are formed into a paste. However, when the mixing amount of the thickening agent in the glass ionomer cement composition is increased, there is such a tendency that a set body thereof is decreased in mechanical strength, such as compressive strength. Therefore, it is the current situation that a paste glass ionomer cement composition using no polymerizable monomer has not yet been in practical use.

SUMMARY OF THE INVENTION

An object of the present invention is to provide a glass ionomer cement composition in paste type using no polymerizable monomer, that is good in operationality with excellent inherent characteristics of glass ionomer cement being maintained.

As a result of earnest investigations made by the inventors, it has been found that a glass ionomer cement composition in paste type having excellent operationality can be obtained by using a first paste containing an $\alpha$-$\beta$ unsaturated carboxylic acid and water and a second paste containing fluoroaluminosilicate glass powder, water and a small amount of a water soluble thickening agent. Therefore, the excellent characteristics of glass ionomer cement can be utilized at the most by using no polymerizable monomer, and thus the present invention has been completed.

The present invention relates to, as one aspect, a paste type dental glass ionomer cement composition comprising: a first paste containing 30 to 70% by weight of a polymer of an $\alpha$-$\beta$ unsaturated carboxylic acid and 30 to 70% by weight of water; and a second paste containing 50 to 85% by weight of fluoroaluminosilicate glass powder, 0.005 to 1% by weight of a water soluble thickening agent and the remaining percentage by weight balance of water. The amount of the water soluble thickening agent is preferably 0.01 to 0.4% by weight.

DETAILED DESCRIPTION OF THE PREFERRED EMBODIMENTS

The polymer of an $\alpha$-$\beta$ unsaturated carboxylic acid used in the first paste of the paste type dental glass ionomer cement composition of the present invention is not particularly limited and may be polymers of an $\alpha$-$\beta$ unsaturated monocarboxylic acid or an unsaturated dicarboxylic acid. Examples thereof include copolymers and homopolymers containing at least one selected from acrylic acid, methacrylic acid, 2-chloroacrylic acid, 3-chloroacrylic acid, aconitic acid, mesaconic acid, maleic acid, itaconic acid, fumaric acid, glutaconic acid and citraconic acid, and preferred examples thereof include polymers having a weight average molecular weight of 5,000 to 40,000 containing no polymerizable ethylenic unsaturated double bond. In the polymer of an $\alpha$-$\beta$ unsaturated carboxylic acid, when the weight average molecular weight is less than 5,000, there is such a tendency that the strength of the hardened composition is lowered and the adhesion property to teeth is lowered. When the weight average molecular weight exceeds 40,000, there is such a tendency that the viscosity upon mixing becomes too large to make mixing difficult. The proportion of the polymer of an α-β unsaturated carboxylic acid in the first paste is necessarily 30 to 70% by weight. When the proportion is less than 30% by weight, the adhesion property to teeth, which is a characteristic feature of the dental glass ionomer, is lowered, and when it exceeds 70% by weight, the viscosity of the paste is increased to lower the mixing property and the operationality.

Water used in the first paste and the second paste of the paste type dental glass ionomer cement composition of the present invention is necessary for the neutralization reaction of the polymer of an α-β unsaturated carboxylic acid used in the first paste and the fluoroaluminosilicate glass powder used in the second paste described later. The proportion of water contained in the first paste is 30 to 70% by weight. When the amount is less than 30% by weight, the viscosity of the paste becomes too high to lower the operationality, and when it exceeds 70% by weight, the adhesion property to teeth, which is a characteristic feature of the dental glass ionomer, is lowered. The proportion of water contained in the second paste is the remaining percentage by weight other than those of the fluoroaluminosilicate glass powder and the water soluble thickening agent, which are constitutional components of the second paste. When the proportion of water is too small, the adhesion property to teeth, which is a characteristic feature of the dental glass ionomer, is lowered, and when it is too large, there is such a tendency that the physical properties of the set body are deteriorated.

Examples of the fluoroaluminosilicate glass powder used in the second paste of the paste type dental glass ionomer cement composition of the present invention include fluoroaluminosilicate glass powder produced by a known process, such as the process disclosed in Japanese Patent Publication No. JP27047/1994, in which silica and alumina are used as major components, to which calcium fluoride, aluminum fluoride, aluminum phosphate and the like are added, and the mixture is cooled and then pulverized.

The fluoroaluminosilicate glass powder used in the second paste of the paste type dental glass ionomer cement composition of the present invention preferably has an average particle diameter of 0.02 to 10 μm and a specific gravity of 2.4 to 4.0. When the average particle diameter exceeds 10 μm, surface smoothness cannot be obtained by grinding to provide adverse feeling in the oral cavity, and when it is fine powder having an average particle diameter of less than 0.02 μm, there is such a possibility that the absolute amount of the powder to be incorporated is decreased to deteriorate the physical properties. The particle diameter can be measured in an ordinary manner and is an average value of a major diameter and a minor diameter.

The fluoroaluminosilicate glass powder is used in the second paste in an amount of 50 to 85% by weight. When the amount is less than 50% by weight, the physical properties of the set composition are deteriorated, and when it exceeds 85% by weight, the second paste becomes too viscous to deteriorate the operationality upon mixing.

In the paste type dental glass ionomer cement composition of the present invention, a water soluble thickening agent is used to obtain a paste having high operationality in the second paste without the use of a polymerizable monomer. The water soluble thickening agent is necessarily used in such a small mixing amount that does not influence the physical property, specifically, in an amount of 1% by weight or less, and preferably 0.4% by weight or less, in the second paste. Specifically, a water soluble thickening agent having such a thickening effect is preferred that an aqueous solution thereof having a concentration of 1% by weight exhibits a viscosity of 500 to 10,000 mPa·s upon measuring at 25° C. with a B-type viscometer. When a thickening agent, a 1% by weight aqueous solution of which exhibits a viscosity of less than 500 mpa·s upon measuring at 25° C. with a B-type viscometer, is used, the sufficient thickening effect cannot be obtained with a small mixing amount. When a thickening agent, a 1% by weight aqueous solution of which exhibits a viscosity exceeding 10,000 mPa·s upon measuring at 25° C. with a B-type viscometer, is used, there is such a tendency that the mixing property of the paste is deteriorated.

The water soluble thickening agent used in the present invention may be either an inorganic one or an organic one, and examples thereof include carboxymethyl cellulose calcium, carboxymethyl cellulose sodium, starch, starch sodium glycolate, starch sodium phosphate, methylcellulose, sodium polyacrylate, alginic acid, sodium alginate, alginic acid propylene glycol ester, casein, sodium casein, polyethylene glycol, ethylcellulose, hydroxyethylcellulose, gluten, locust bean gum and gelatin. Among these, carboxymethyl cellulose calcium and carboxymethyl cellulose sodium are preferred since they are inexpensive and exert high thickening effect with a small amount. The water soluble thickening agent may be used as a mixture of two or more kinds thereof. The amount of the water soluble thickening agent in the second paste is preferably 0.005 to 1% by weight. When the amount is less than 0.005% by weight, the effect by the thickening agent cannot be obtained, and when it exceeds 1% by weight, there is such a tendency that the strength of the hardened composition is lowered. Furthermore, the mixing amount of the water soluble thickening agent is preferably as small as possible to prevent the hardened composition from deterioration of the physical property, and thus, it more preferably contains in the second paste in an amount of 0.01 to 0.4% by weight.

In the paste type dental glass ionomer cement composition of the present invention, an antibacterial agent and a coloring agent, such as a pigment, which are ordinarily used in this field of art, may be appropriately mixed depending on necessity.

EXAMPLES

The present invention will be described in more detail below with reference to the following examples.

Fluoroaluminosilicate Glass Powder A 22 g of aluminum oxide, 23 g of anhydrated silica, 12 g of calcium fluoride, 15 g of calcium phosphate and 28 g of strontium fluoride were sufficiently mixed in a mortar, and the resulting batch was placed in a porcelain crucible. The batch was heated in an electric furnace to 1,200° C. at a temperature increasing rate of about 7° C. per minute, and maintained at that temperature for 3 hours. The resulting molten liquid was poured into water to obtain quenched glass, which was then pulverized to obtain fluoroaluminosilicate glass powder A. The powder had an average particle diameter of 2.5 μm.

Fluoroaluminosilicate Glass Powder B 23 g of aluminum oxide, 31 g of anhydrated silica, 1 g of calcium fluoride, 9 g of cryolite, 2 g of aluminum phosphate and 34 g of strontium fluoride were sufficiently mixed in a mortar, and the resulting batch was placed in a porcelain crucible. The batch was heated in an electric furnace to 1,200° C. at a temperature increasing rate of about 7° C. per minute, and maintained at that temperature for 3 hours. The resulting molten liquid was poured into water to obtain quenched glass, which was then pulverized to obtain fluoroaluminosilicate glass powder B. The powder had an average particle diameter of 2.5 μm.

Examples 1 to 8 and Comparative Examples 1 to 2

Several kinds of carboxymethyl cellulose sodium (Cellogen, a trade name, produced by Dai-ichi Kogyo Seiyaku Co., Ltd.) of model numbers shown in Table 2 were used as the water soluble thickening agent, and paste type dental glass ionomer cement compositions were prepared with the mixing compositions shown in Table 1. 1.0 g of the first paste and 1.3 g of the second paste were weighed and mixed on a mixing paper by using a spatula for 15 second, at which the operationality was evaluated, and the following tests were carried out.

Compressive Strength

A sample after mixing was charged in a metallic split mold having an inner diameter of 4 mm and a height of 6 mm, and the upper and lower bottoms were sealed with metallic plates and compressed and fixed with a clamp. The assembly was allowed to stand in an atmosphere of a temperature of 37° C. and a humidity of 100% for one hour to carry out hardening. The set composition was released from the split mold, and the resulting cylindrical sample was immersed in distilled water at 37° C. for 24 hours. Thereafter, the sample was subjected to a compression test with a universal testing machine (Autograph, a trade name, produced by Shimadzu Corp.) under the condition of a crosshead speed of 1 mm/min. The results obtained are shown in Table 1.

Adhesion Strength

A tooth root was cut from an anterior tooth of a lower jaw of bovine, and the tooth was polished with water proof paper #600 to expose dentin for adhesion of the sample. A masking tape having a hole of a diameter of 3 mm was attached to the dentin surface of a bovine tooth, and the sample after mixing was placed on the hole. A stainless steel bar was pressed and stood on the sample, and the sample was allowed to stand in an atmosphere of a temperature of 37° C. and a humidity of 100% for one hour and then immersed in distilled water at 37° C. for 24 hours. Thereafter, the sample was pulled with a universal testing machine (Autograph, a trade name, produced by Shimadzu Corp.) under the condition of a crosshead speed of 1 mm/min to measure the adhesion strength. The results obtained are shown in Table 1.

TABLE 1

Compositions of paste type dental glass ionomer cement compositions (% by weight)

| | | | Example 1 | Example 2 | Example 3 | Example 4 | Example 5 |
|---|---|---|---|---|---|---|---|
| First paste | Polymer of α-β unsaturated carboxylic acid | Copolymer (*1) | 50 | 50 | 41 | — | — |
| | | Homopolymer (*2) | — | — | — | 50 | 60 |
| | Distilled water | | 50 | 50 | 59 | 50 | 40 |
| Second paste | Fluoroalumino-silicate glass powder | Glass A | 75 | 80 | 60 | 75 | 79 |
| | | Glass B | — | — | — | — | — |
| | Thickening agent | CMCNa F-SA | 0.05 | — | — | — | '3 |
| | | CMCNa HF-600F | — | 0.05 | — | — | — |
| | | CMCNa F-3H | — | — | 0.05 | — | — |
| | | CMCNa F-BSH-4 | — | — | — | 0.05 | 0.20 |
| | Distilled water | | 24.95 | 19.95 | 39.95 | 24.95 | 20.80 |
| Operationality | | | good | good | good | good | good |
| Compression strength (MPa) | | | 72 | 88 | 71 | 79 | 86 |
| Adhesion strength (MPa) | | | 4.5 | 4.8 | 5.2 | 5.2 | 4.9 |

| | | | Example 6 | Example 7 | Example 8 | Comparative Example 1 | Comparative Example 2 |
|---|---|---|---|---|---|---|---|
| First paste | Polymer of α-β unsaturated carboxylic acid | Copolymer (*1) | 53 | 55 | 38 | 53 | 50 |
| | | Homopolymer (*2) | — | — | — | — | — |
| | Distilled water | | 47 | 45 | 62 | 47 | 50 |
| Second paste | Fluoroalumino-silicate glass powder | Glass A | 79 | — | — | 79 | 69 |
| | | Glass B | — | 70 | 75 | — | — |
| | Thickening agent | CMCNa F-SA | — | 0.05 | — | 0.001 | 10 |
| | | CMCNa HF-600F | — | — | — | — | — |
| | | CMCNa F-3H | — | — | 0.05 | — | — |
| | | CMCNa F-BSH-4 | 0.20 | — | — | — | — |
| | Distilled water | | 20.80 | 29.95 | 24.95 | 20.999 | 21.00 |
| Operationality | | | good | good | good | Paste not formed | good |
| Compression strength (MPa) | | | 88 | 76 | 81 | | 24 |
| Adhesion strength (MPa) | | | 4.8 | 5.1 | 5.5 | | 3.0 |

Note:
*1 Acrylic acid-itaconic acid copolymer (weight average molecular weight: 24,000)
*2 Acrylic acid homopolymer (weight average molecular weight: 16,000)

TABLE 2

| Model number of CMCNa | Viscosity of 1% aqueous solution (at 25° C., B-type viscometer) |
|---|---|
| F-SA | 800 mPa · s |
| HF-600F | 10,000 mPa · s |
| F-3H | 1,000 mPa · s |
| F-BSH-4 | 2,500 mPa · s |

CMCNa: carboxymethyl cellulose sodium (Cellogen, a trade name, produced by Dai-ichi Kogyo Seiyaku Co., Ltd.)

Dental paste glass ionomer cement compositions having good operationality could be obtained in Examples 1 to 8. In Comparative Example 1, in which the amount of the water soluble thickening agent in the second paste was as small as 0.001% by weight, a glass ionomer cement composition in paste type could not be obtained. In Comparative Example 2, in which the amount of the thickening agent was as large as 10% by weight, a glass ionomer cement composition in paste type having good operationality was obtained, but the mechanical strength, such as compression strength, of the hardened composition was inferior to the dental paste glass ionomer cement of Examples.

As apparent from Examples and Comparative Examples, in the paste type dental glass ionomer cement composition of the present invention, the second paste containing fluoroaluminosilicate glass can be in paste form without the use of a polymerizable monomer. Furthermore, the paste type dental glass ionomer cement composition does not suffer decrease in physical strength upon hardening by mixing the first and second paste, and exhibits excellent adhesion property that is equivalent to that of the conventional glass ionomer cement. Therefore, the value of the dental paste glass ionomer cement composition of the present invention contributing in the field of dental surgery is considerably large.

What is claimed is:

1. A paste type dental glass ionomer cement composition comprising:
    a first paste containing 30 to 70% by weight of a polymer of an α-β unsaturated carboxylic acid and 40 to 70% by weight of water; and
    a second paste containing 50 to 85% by weight of fluoroaluminosilicate glass powder, 0.005 to 1% by weight of a water soluble thickening agent and the remaining percentage by weight of water, wherein
    the water soluble thickening agent is an inorganic thickening agent or is selected from the group consisting of carboxymethyl cellulose calcium, carboxymethyl cellulose sodium, starch, starch sodium glycolate, starch sodium phosphate, methylcellulose, sodium polyacrylate, alginic acid, sodium alginate, alginic acid propylene glycol ester, casein, sodium casein, polyethylene glycol, ethylcellulose, hydroxyethylcellulose, gluten, locust bean gum, gelatin and mixtures thereof.

2. A paste type dental glass ionomer cement composition as claimed in claim 1, wherein an amount of the water soluble thickening agent is 0.01 to 0.4% by weight.

3. The paste type dental glass ionomer cement composition of claim 1, wherein the polymer of an α-β unsaturated carboxylic acid comprises a polymer of an α-β unsaturated monocarboxylic acid.

4. The paste type dental glasss ionomer cement composition of claim 1, wherein the polymer of an α-β unsaturated carboxylic acid comprises a polymer of an α-β unsaturated dicarboxylic acid.

5. The paste type dental glass ionomer cement composition of claim 1, wherein the polymer of an α-β unsaturated carboxylic acid comprises copolymer and homopolymers containing at least one monomer selected from the group consisting of acrylic acid, methacrylic acid, 2-chloroacrylic acid, 3-chloroacrylic acid, aconitic acid, mesaconic acid, maleic acid, itaconic acid, fumaric acid, glutaconic acid and citraconic acid.

6. The paste type dental glass ionomer cement composition of claim 1, wherein the polymer of an α-β unsaturated carboxylic acid is a polymer having a weight average molecular weight of from 5,000 to 40,000 not containing a polymerizable ethylenic unsaturated double bond.

7. The paste type dental glass ionomer cement composition of claim 1, wherein the fluoroaluminosilicate glass powder has an average particle diameter of from 0.02 to 10 μm.

8. The paste type dental glass ionomer cement composition of claim 1, wherein the fluoroaluminosilicate glass powder has a specific gravity of from 2.4 to 4.0.

9. The paste type dental glass ionomer cement composition of claim 1, wherein the water soluble thickening agent is an inorganic thickening agent.

10. The paste type dental glass ionomer cement composition of claim 1, wherein the water soluble thickening agent is selected from the group consisting of carboxymethyl cellulose calcium, carboxymethyl cellulose sodium, starch, starch sodium glycolate, starch sodium phosphate, methylcellulose, sodium polyacrylate, alginic acid, sodium alginate, alginic acid propylene glycol ester, casein, sodium casein, polyethylene glycol, ethylcellulose, hydroxyethylcellulose, gluten, locust bean gum, gelatin and mixtures thereof.

11. The paste type dental glass ionomer cement composition of claim 1, further comprising antibacterial agent, coloring agent or mixtures thereof.

12. The paste type dental glass ionomer cement composition of claim 11, wherein the coloring agent is a pigment.

* * * * *